(12) United States Patent
Matschofsky et al.

(10) Patent No.: US 10,589,321 B2
(45) Date of Patent: Mar. 17, 2020

(54) METHOD OF, AND AN APPARATUS FOR, RINSING MATERIALOGRAPHIC SAMPLES

(71) Applicant: Struers ApS, Ballerup (DK)

(72) Inventors: Thomas Matschofsky, Albertslund (DK); Palle Oppelstrup, Ballerup (DK)

(73) Assignee: Struers ApS, Ballerup (DK)

(*) Notice: Subject to any disclaimer, the term of this patent is extended or adjusted under 35 U.S.C. 154(b) by 336 days.

(21) Appl. No.: 15/305,797

(22) PCT Filed: Apr. 23, 2015

(86) PCT No.: PCT/EP2015/058750
§ 371 (c)(1),
(2) Date: Oct. 21, 2016

(87) PCT Pub. No.: WO2015/162194
PCT Pub. Date: Oct. 29, 2015

(65) Prior Publication Data
US 2017/0043380 A1  Feb. 16, 2017

(30) Foreign Application Priority Data
Apr. 24, 2014 (DK) .................. 2014 70240

(51) Int. Cl.
*B08B 3/12* (2006.01)
*G01N 1/34* (2006.01)
(Continued)

(52) U.S. Cl.
CPC .............. *B08B 3/12* (2013.01); *B08B 3/10* (2013.01); *G01N 1/32* (2013.01); *G01N 1/34* (2013.01);
(Continued)

(58) Field of Classification Search
CPC ... B08B 3/12; B08B 3/10; G01N 1/32; G01N 1/34; H01L 21/67057; H01L 21/68721;
(Continued)

(56) References Cited

U.S. PATENT DOCUMENTS 5,698,038 A  12/1997  Guldi et al.
5,985,811 A  11/1999  Masayuki et al.
(Continued)

FOREIGN PATENT DOCUMENTS

CN  103447937 A  12/2013

OTHER PUBLICATIONS

Kay Geels, "Metallographic and Materialographic Specimen Preparation, Light Microscopy, Image Analysis and Hardness Testing", ASTM standard; Lancaster, Pennsylvania, US, Jun. 2007, section 5.1.2 (pp. 82-83).

*Primary Examiner* — Sharidan Carrillo
(74) *Attorney, Agent, or Firm* — Snyder, Clark, Lesch & Chung, LLP (57) ABSTRACT

The present invention relates to a method of, and an apparatus for, rinsing materialographic samples. The method includes the steps of:
  arranging one or more materialographic samples in a sample holder;
  connecting the sample holder (10) to a rotation head of a rinsing device;
  placing the sample holder connected to the rotation head in the vessel of the rinsing device;
  rotating the sample holder relative to the vessel;
  filling the vessel with a rinsing liquid; and
  subjecting the materialographic samples in the sample holder to ultrasonic waves.

17 Claims, 7 Drawing Sheets

(51) Int. Cl.
*H01L 21/67* (2006.01)
*H01L 21/687* (2006.01)
*G01N 1/32* (2006.01)
*B08B 3/10* (2006.01)

(52) U.S. Cl.
CPC .. *H01L 21/67057* (2013.01); *H01L 21/68721* (2013.01); *H01L 21/68764* (2013.01); *H01L 21/68771* (2013.01); *H01L 21/68792* (2013.01)

(58) Field of Classification Search
CPC ......... H01L 21/68764; H01L 21/68771; H01L 21/68792
See application file for complete search history.

(56) References Cited

U.S. PATENT DOCUMENTS

| | | |
|---|---|---|
| 6,247,198 B1 | 6/2001 | Kobayashi et al. |
| 6,684,890 B2 * | 2/2004 | Nicolosi .................. B08B 3/12 134/1 |
| 7,317,964 B1 | 1/2008 | Spowart et al. |
| 2004/0007257 A1 * | 1/2004 | Park .......................... B08B 3/12 134/95.2 |
| 2004/0163682 A1 | 8/2004 | Boyd et al. |
| 2008/0029123 A1 * | 2/2008 | Aegerter ........... H01L 21/67051 134/1 |
| 2009/0079122 A1 * | 3/2009 | Obweger .......... H01L 21/67051 269/57 |
| 2016/0027680 A1 * | 1/2016 | Tschinderle ...... H01L 21/67051 156/345.23 |

* cited by examiner

METHOD OF, AND AN APPARATUS FOR, RINSING MATERIALOGRAPHIC SAMPLES

The present invention relates, according to a first aspect, to a method of rinsing/cleaning materialographic specimens such as cylindrical materialographic samples. In particular, the first aspect relates to a method of cleaning metallographic samples.

According to a second aspect, the present invention relates to a rinsing apparatus configured for rinsing materialographic samples.

BACKGROUND OF THE INVENTION

In connection with obtaining materialographic samples, pieces of a material, e.g. a metal, are cut by abrasive cut off wheels in, for example, materialographic cutting machines, such as metallographic cutting machines.

After a sample has been cut by a cut off wheel, the sample needs to be prepared for examination by one or more of grinding, lapping and polishing a surface of the sample often in a stepwise finer manner.

Grinding may be defined as the rapid and often initial removal of material from a specimen either to reduce the specimen to a suitable size or to remove large irregularities from the surface.

Lapping may be defined as the removal of material to produce a smooth, flat, unpolished surface. Lapping processes are used to produce dimensionally accurate specimens to high tolerances.

Polishing may be defined as is the removal of material to produce a scratch-free, specular surface. Polishing is typically done at very low speeds using either polishing cloths, abrasive films, or specially designed lapping plates.

Prior to preparation for examination, the samples are placed in, or molded in, a base for easy handling. The base may constitute a sample holder.

For the purpose of obtaining and examining e.g. metallographic samples, which typically are cylindrical, test objects are, as mentioned above, prepared by one or more of grinding, lapping and subsequently polishing. In between each step, the metallographic sample needs to be rinsed to remove coarse-grained debris and abrasives before the next and finer step to avoid contaminating the following preparation procedure.

The normal procedure for rinsing such metallographic samples typically involves manually transferring the metallographic sample to a sink, washing the metallographic sample in a special soap, then in alcohol/methylated spirit, and manually drying the metallographic sample, either using a cloth, blow drying, or both. This procedure is described in e.g. the ASTM standard; Geels, Kay: "Metallographic and Materialographic Specimen Preparation, Light Microscopy, Image Analysis and Hardness Testing"; Lancaster, Pa., US, June 2007, section 5.1.2 (pages 82-83).

It is a problem of the prior art that these actions are hard to perform without getting smeared, and there is a risk of contaminating the sample. Further, it is difficult or not possible to obtain a constant quality of rinsing, whereby, replicability in the sampling procedure is diminished. Yet further, the handling of special soap or alcohol is at risk of inducing health and environmental problems. Yet further, it is hard to control the use of water, soap and alcohol in the manual process, often causing excess use, which increases the cost and waste product, the latter, especially, being a potential environmental problem.

Also known in the art is a machine where a number of metallographic samples are placed in a holder and where the samples are stepwise ground/polished. In between each step, an arm transports the holder with the metallographic sample from the grinding site to a chamber filled with soap water, submerging the holder into the soap solution, and subjecting the holder with the metallographic samples to ultrasonic waves. Subsequently, the arm extracts and transports the metallographic sample from the soap solution chamber and into a separate chamber, wherein clean water under pressure is sprayed on the soap-water soaked holder with the samples to rinse of the soap and any debris on the holder and metallographic samples. Finally, in the same chamber, the holder and the metallographic samples are dried by pressurized air. Such a machine is provided by the applicant under the name Hexamatic and MAPS.

It is a problem, with the prior art device that it uses larger quantities of detergents/chemicals, and relatively large quantities of energy for drying.

Further, despite being a fully automated device, the process is slow if the rinsing quality is to be kept sufficiently high. Under section 5.1.2 the ASTM standard; Geels, Kay: "Metallographic and Materialographic Specimen Preparation, Light Microscopy, Image Analysis and Hardness Testing"; Lancaster, Pa., US, June 2007, also mentions the use of ultrasound to clean specimens, where the specimens are placed in a tank filled with water with a detergent, alcohol or organic solvent. In cases where the samples are particularly dirty, Geels suggest to use weak acids or basic solutions.

U.S. Pat. No. 5,985,811 A discloses a method of spray cleaning semiconductors by rotating the material to be cleaned in a cleaning vessel while applying ultrasound to a flow of cleaning liquid being fed to the spraying nozzle. Ultrasound is applied to the cleaning liquid with the purpose of generating free radicals in order to facilitate cleaning the semiconductors.

U.S. Pat. No. 7,317,964 B1 discloses a method of 3D high precision reconstruction of microstructure specimens.

CN 103447937 A discloses an automatic grinding and polishing machine. According to the reference, after polishing of the samples is completed, the samples are moved into an ultrasonic washing box to carry out washing of the samples.

U.S. Pat. No. 6,247,198 B discloses an apparatus for cleaning a wafer. The wafer is cleaned by brushes and placed in a cleaning liquid. Furthermore, ultrasonic vibrations are applied to the cleaning liquid by an ultrasonic generator.

US 2004/163682 A discloses a method for cleaning a semiconductor. The method initiates with generating acoustic energy oriented in a substantially perpendicular direction to a surface of a semiconductor substrate. Then, acoustic energy oriented in a substantially parallel direction to the surface of the semiconductor substrate is generated.

SUMMARY OF THE INVENTION

On this background, it is an object of the present invention to provide a more efficient, reliable and consistent method of, and apparatus for; rinsing materialographic samples, which at the same time uses fewer resources such as detergents and other chemicals. Such materialographic samples are samples, which are cut from a specimen and prepared by grinding and subsequently polishing the sample in a number of steps, using stepwise finer grinding and polishing. The grinding and polishing of such samples is performed using ever finer grain size in the range of 250 µm to 0.1 μm. For polishing, normally 0.1-35 μm grain size is used and for grinding 10-250 μm grain size. Materialographic samples may be most types of solid materials (polymer, ceramic, composite, electronic, etc.). In particular it is an object to provide a method of rinsing metallographic samples.

This object is achieved by a method of rinsing materialographic samples (1) including, in an arbitrary or sequential order, the steps of:
   arranging one or more materialographic samples to be rinsed in a sample holder,
   coupling the sample holder to a rotation head of a rinsing apparatus,
   placing the sample holder coupled to the rotation head in a vessel (20) of the rinsing apparatus,
followed by, in a sequential order or not, the steps of:
   commencing filling the vessel with a rinsing liquid by injecting rinsing liquid through an inlet (26) provided in the bottom of the vessel (20) thereby submerging the samples into the rinsing liquid;
   subjecting the rinsing liquid and the materialographic samples to ultrasound, and
   rotating the sample holder incl. materialographic samples relative to the vessel.
wherein the step of subjecting the rinsing liquid and the materialographic samples (1) to ultrasound is maintained at least during filling of the vessel (20) with rinsing liquid The application of ultrasound prior to commencing rotation of the sample holder allows for rinsing of the samples by means of ultrasound via substantially stagnant rinsing liquid. By this, increased rinsing efficiency is provided. Furthermore, as the rinsing efficiency is increased, omission of rinsing agents is rendered possible. Finally, by this, the rinsing process may take place in tap water.

By rotating the sample holder while applying ultrasound, it furthermore has surprisingly been found that the rinsing of materialographic samples can be shortened time-wise, while a more stable rinsing result is obtained. Further, the method according to the invention allows the rinsing to occur quickly and with a greatly reduced or even eliminated consumption of detergents. It has been found that even pure water, or tap water, may be used as rinsing liquid. In the context of the present application, by pure water is meant tap water without any additives, such as detergents, alcohol, or organic solvents, e.g. acetone, or weak acids or basic solutions.

In the prior art ultra clean water, desalinated water, or demineralized water is used in combination with detergents, alcohol, or organic solvents. With the invention according to the present method this is not necessary.

Further, the method allows a precise dosing of liquid/water, and reduced or eliminated use of drying with compressed air.

In an embodiment, the step of subjecting the materialographic samples in the sample holder to ultrasonic waves is initiated during the filling of the vessel with rinsing liquid. Thereby it is achieved the eventual residues/dirt from previous uses are loosened early in the rinsing process.

In a further embodiment the rotation of the sample holder is initiated after the ultrasound is initiated.

In yet another embodiment where said rinsing device comprises a lid for covering said vessel, where said method comprises the step of injecting said rinsing liquid through a bottom of said vessel, where the path of said injected rinsing liquid is deflected from a direction parallel to the axis of rotation of the sample holder, and where said injection of rinsing fluid is initiated before a step of closing set said lid is completed.

In yet another embodiment, the method further comprises the step of emptying the rinsing liquid from the vessel while rotating the sample holder in the vessel. In an embodiment hereof the application of ultrasound is maintained during the emptying of the vessel.

In yet another embodiment hereof, the rotational speed of the sample holder is increased upon initiating the emptying of the vessel.

In yet another embodiment hereof, the method further comprises the step of spraying alcohol or methylated spirit on the materialographic samples (1) in the sample holder after emptying the rinsing liquid from the vessel while rotating the sample holder in the vessel.

In yet another embodiment hereof, the vessel is evacuated by applying a vacuum to an outlet of the vessel.

In all of the above mentioned embodiments the rinsing liquid may be pure water.

Further objects, features, advantages and properties of the method for rinsing materialographic samples according to the invention will become apparent from the detailed description.

BRIEF DESCRIPTION OF THE DRAWINGS

In the following detailed portion of the present description, the invention will be explained in more detail with reference to the exemplary embodiments shown in the drawings, in which.

DETAILED DESCRIPTION OF THE INVENTION

In the following detailed description, the method of rinsing materialographic samples and a rinsing device 100 according to the invention will be described by preferred embodiments.

Figure 5:
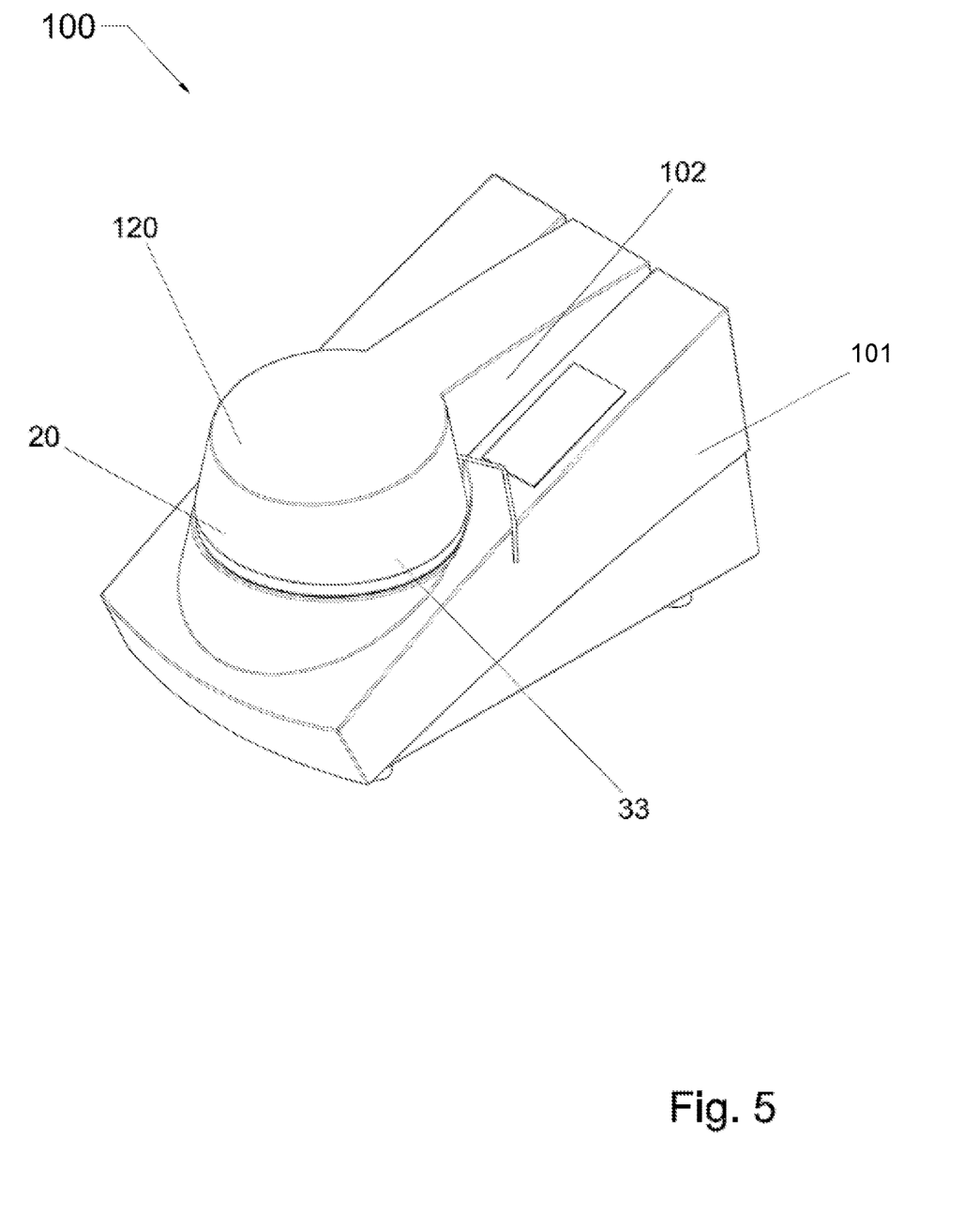
FIG. 5, in a perspective view, shows a rinsing apparatus for use in the method according to the present invention.

In the figures, FIG. 5 shows a rinsing apparatus 100 for performing the method according to the invention. The rinsing apparatus 100 comprises a housing 101. A vessel 20 is arranged in the housing. An arm 102 extending from the housing holds a lid 120, adapted for covering the vessel 20, see further below.

In the embodiment shown in FIG. 5 the arm is pivotally connected to the housing 101. A not shown motor or actuator may be arranged in the housing 101 or in the arm 102, adapted to move the arm 102 between at least two positions, one where the lid 120 covers and closes the vessel 20; and one where access to the vessel 20 is provided.

In other embodiments, the lid 20 may alternatively or additionally be manually operable.

In FIG. 5, the arm 102 further comprises not shown rotational drive means (motors/actuators) for rotating a sample holder 10 (not shown in FIG. 5, see below), which may be coupled to the arm 102.

Figure 2:
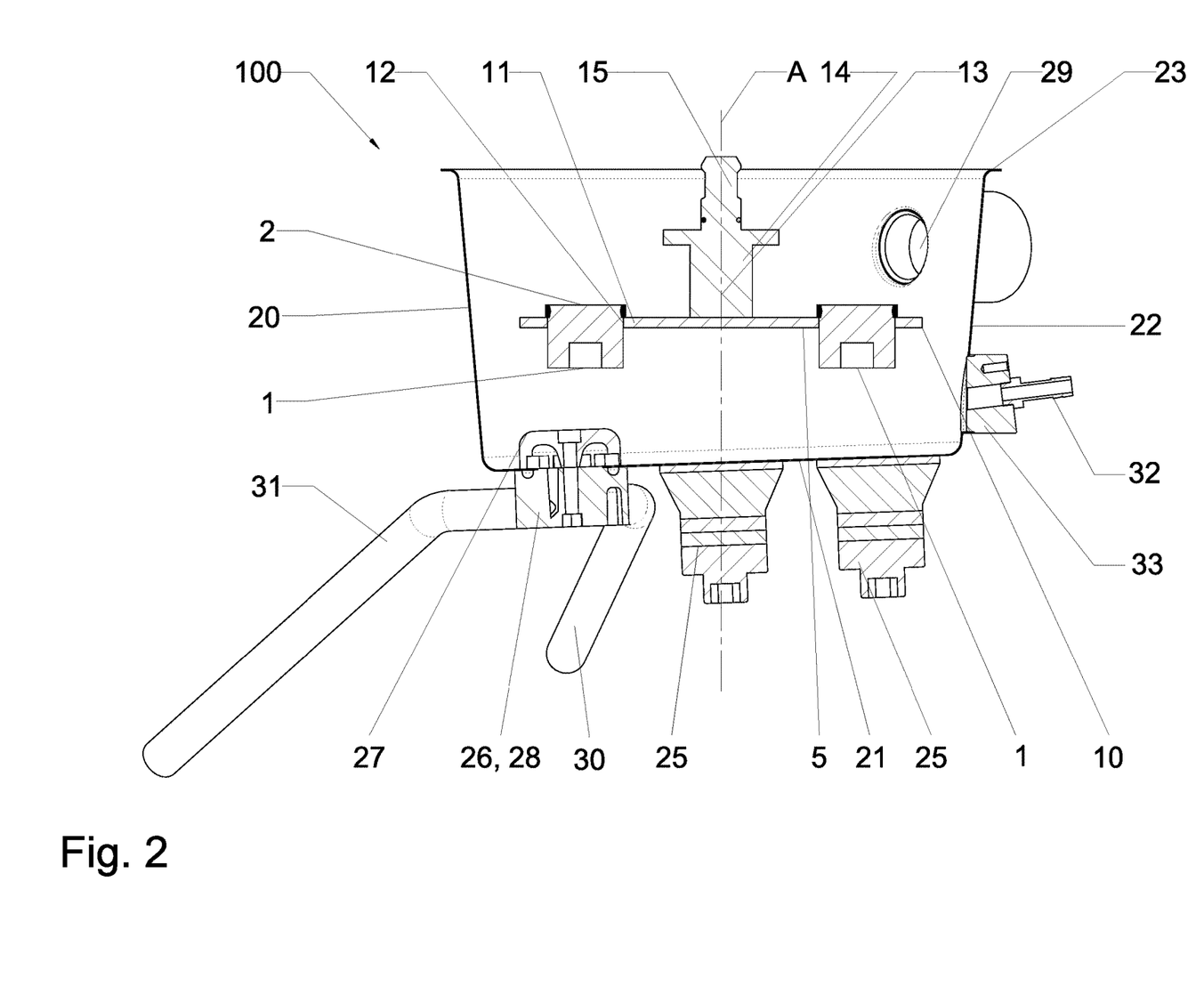
FIG. 2, in a side sectional view, shows details of a rinsing device for use in the method according to the present invention.
Figure 3:
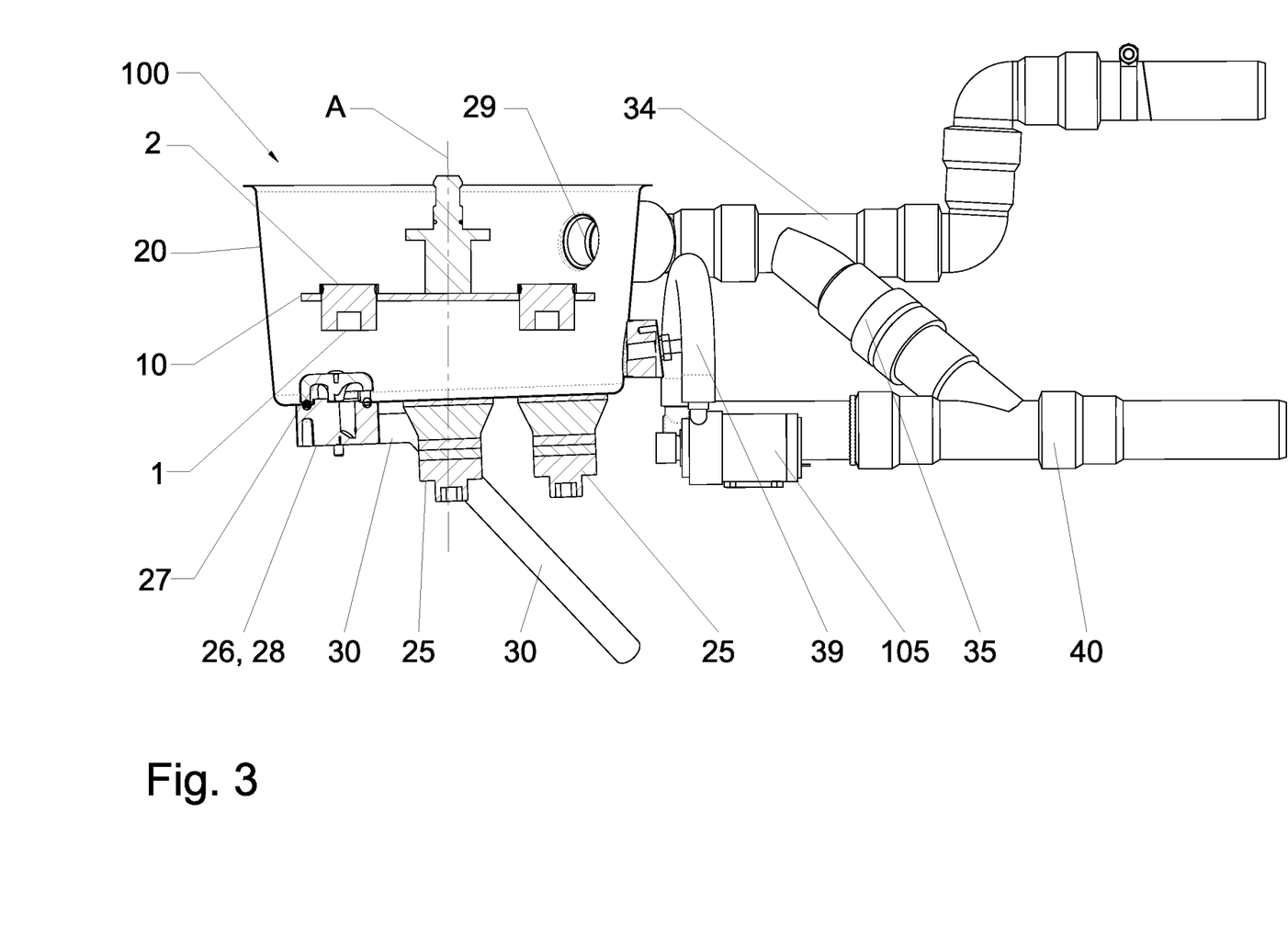
FIG. 3, in a partly sectional side view, shows details of a liquid supply and evacuation system according to one embodiment of the invention.
Figure 4:
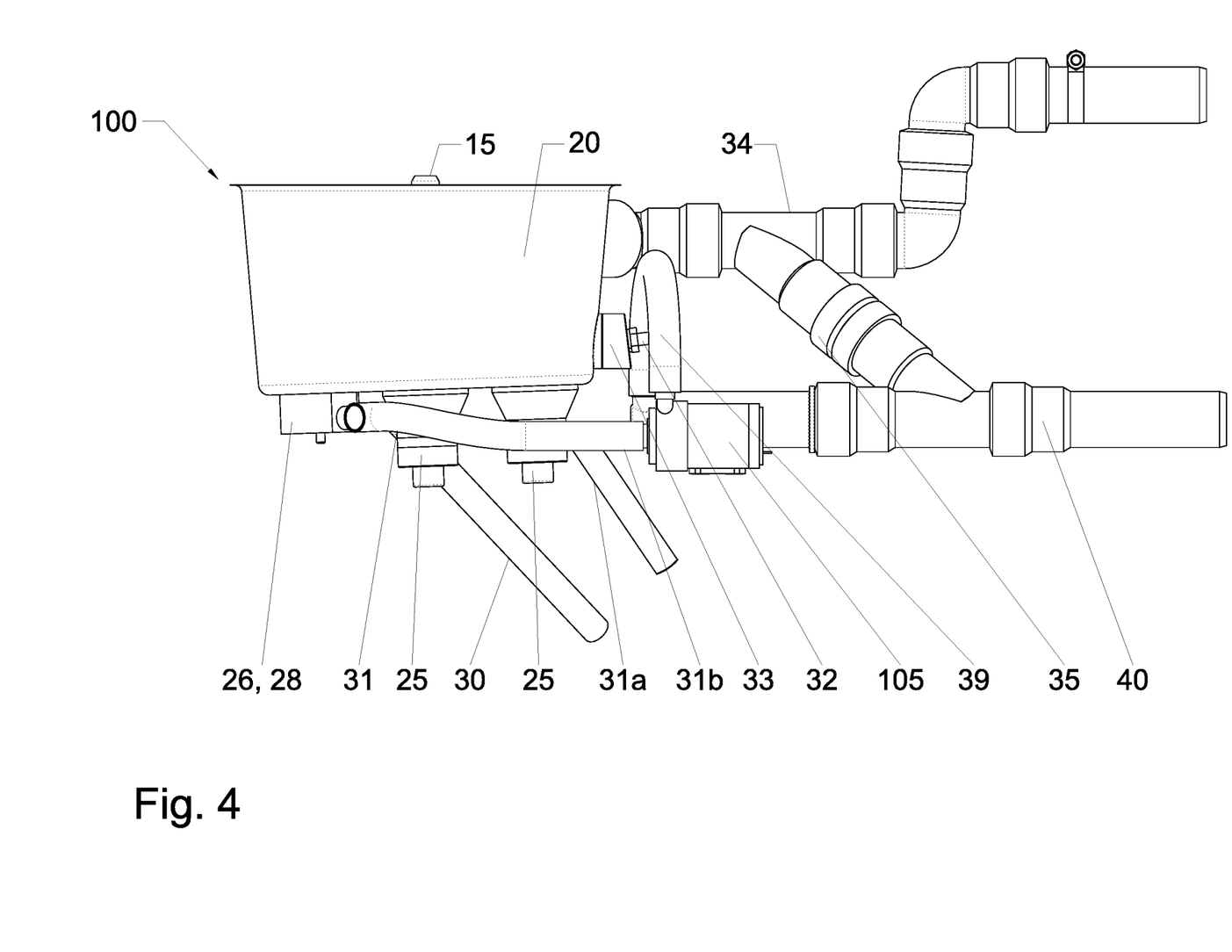
FIG. 4, is a side view of the liquid supply and evacuation system shown in FIG. 3.

FIGS. 2-4 show details of the rinsing device 100 for use in the method according to the invention. For the sake of simplicity, basic components like the housing, drive motors/actuators, etc. have been left out.

In FIG. 2, the rinsing device 100 is partially represented by the vessel 20 and auxiliary components. The vessel 20 is cup-shaped with an open upwardly facing surface defining an interior cavity. The vessel 20 has a bottom 21 and a substantially circular/cylindrical sidewall 22 with an upper edge or rim 23, the substantially circular/cylindrical sidewall 22 extending upward from the bottom 21. The vessel 20 is preferably stationary relative to the housing 101 of the apparatus as per FIG. 5. (the housing is not shown in FIGS. 2-4) The vessel 20 is connected or is connectable to the housing 101 via mounts (not shown) or other suitable means.

The vessel 20 may accommodate a sample holder 10 as shown in FIGS. 2 and 3.

Details of the sample holder 10 are better explained with reference to FIGS. 1, 6 and 7. The sample holder 10 comprises a circular plate 11 formed or provided with a plurality of openings 12 forming receptacles for samples 1 (as shown in FIG. 3) each mounted or locked in a base 2. Thus, each opening 12 is adapted for receipt of a sample 1. The sample 1 therefore comprises a piece of materialographic material locked in a base 2. The base 2 is preferably cylindrical in shape, and adapted for cooperation with the openings 12 of the sample holder 10.

Figure 1:
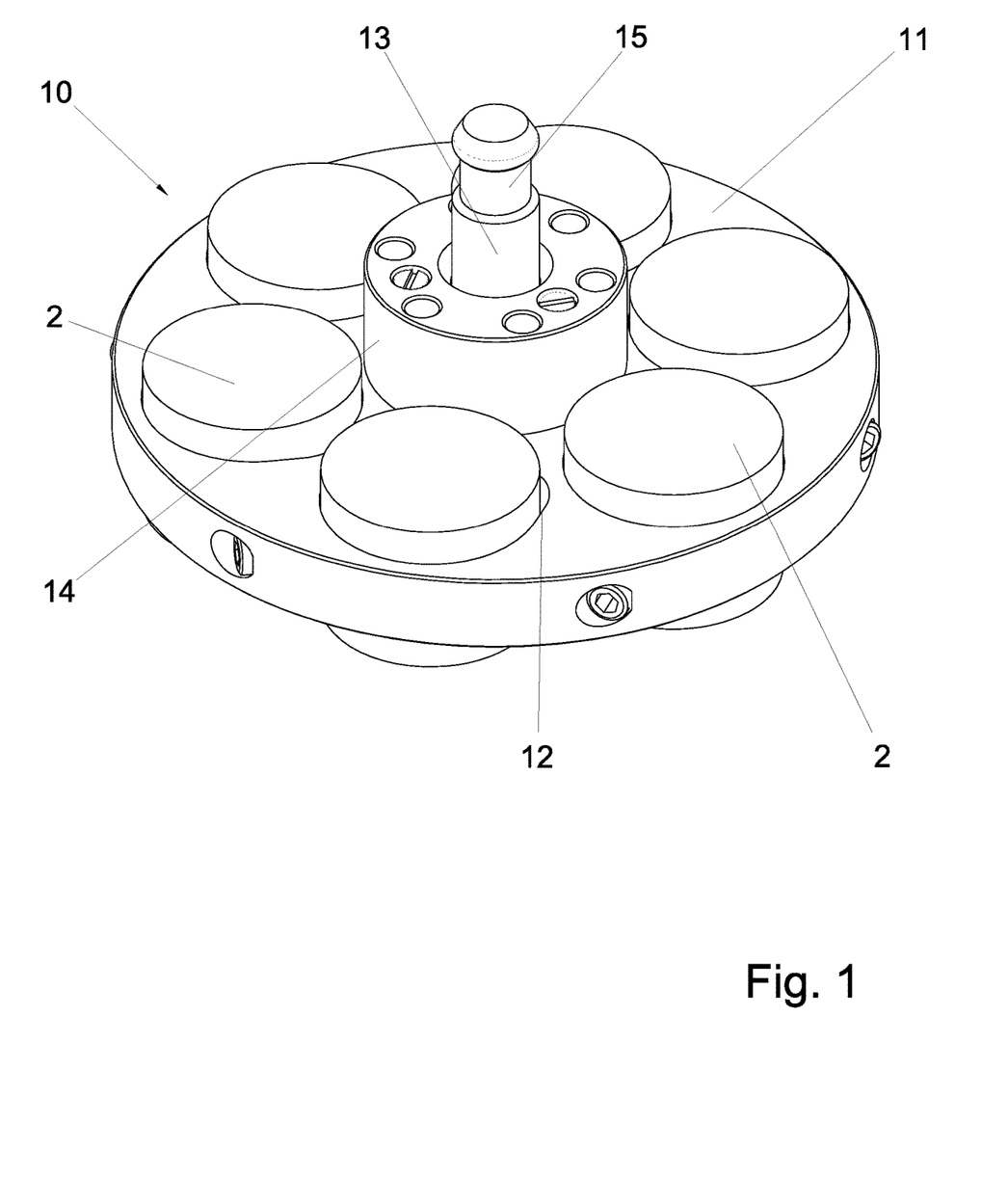
FIG. 1, in a perspective view, shows details of a sample holder with samples for a rinsing device for use in the method according to the present invention.

As shown in FIG. 1 the base 2 may be held in the openings 12 by screws formed in holes, or internal threads, provided in the rim plate 11. In other embodiments, the receptacles/openings 12 and/or the bases 2 may be formed with a resilient material to form a tight fit between the two.

Figure 6:
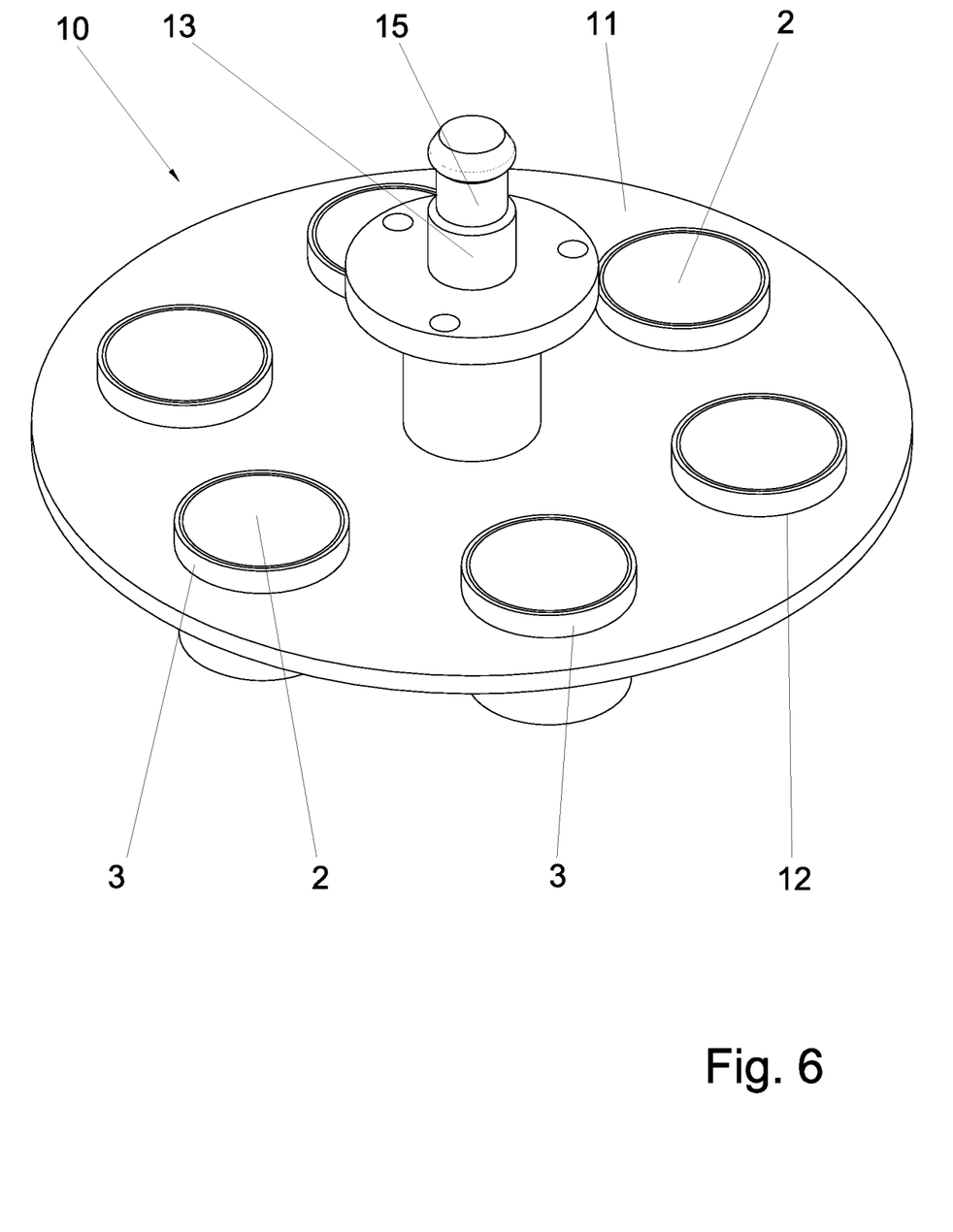
FIG. 6, in a perspective view, shows details of an alternative sample holder with samples for a rinsing device for use in the method according to the present invention.

As shown in FIG. 6, a resilient retention ring 3 may be formed or arranged on the cylindrical base 2 to secure that the sample cannot pass through the hole forming the receptacle 12. The samples 1 and the bases 2 are loosely placed in the receptacle/hole 12. The resilient retention ring 3 has a tight fit to the materialographic sample 1 and the base 2, and thus provides a larger diameter than the hole 12 thereby preventing that the sample 1 cannot pass through the hole 12.

Figure 7:
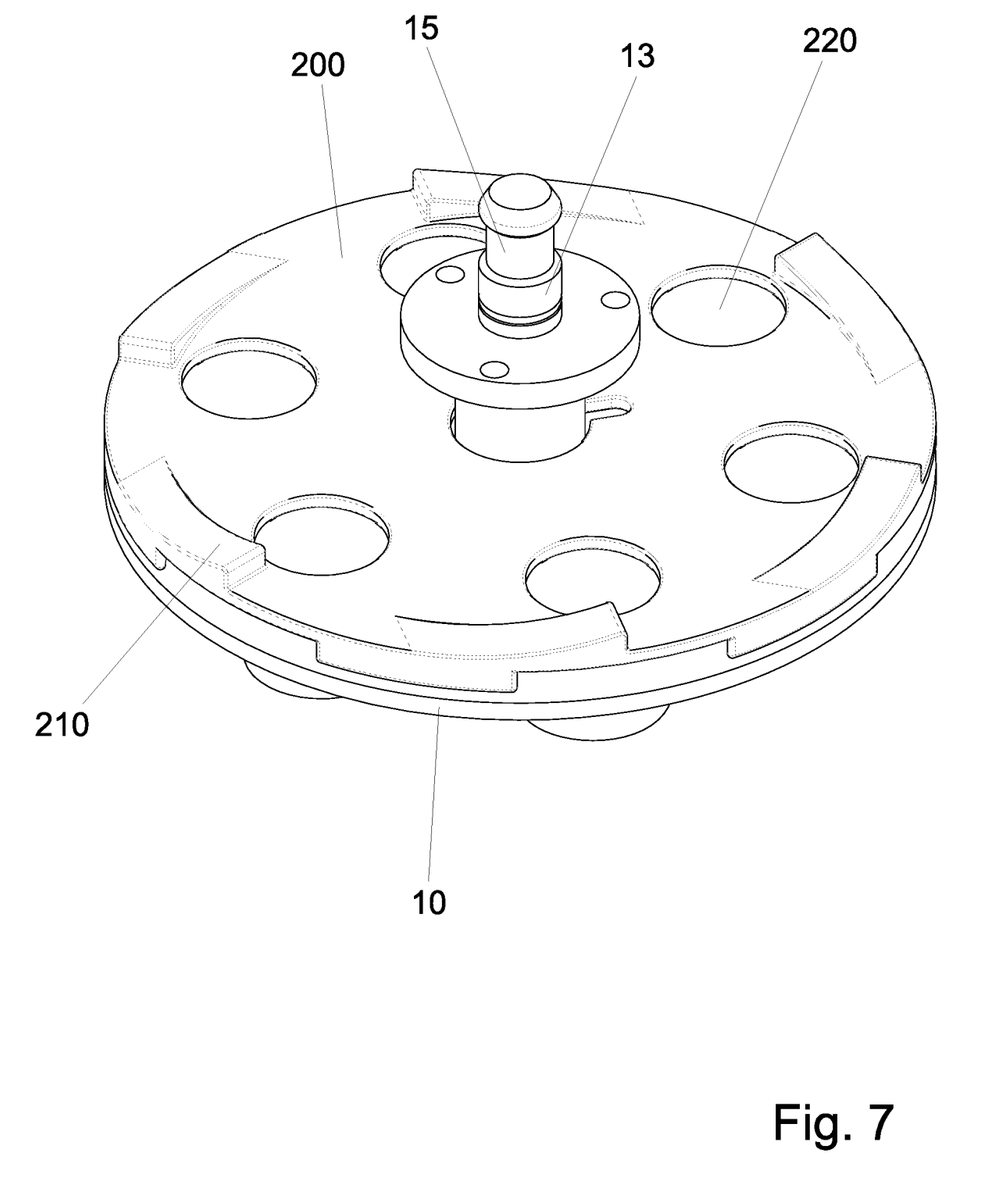
FIG. 7, in a perspective view, shows a retainer plate arranged on an upper face of a sample holder.

FIG. 7 shows an embodiment wherein the samples 2 are retained in the sample holder 10 by means of a retainer plate 200. The retainer plate 200 may be made from a flexible or resilient material such as rubber or equivalent. The retainer plate 200 may be configured to rest on an upper face of the sample holder 10. The retainer plate 200 may be provided with fins 210 configured to urge the underside of the retainer plate 200 against the samples 1/bases 2 under centrifugal force. Furthermore, the retention plate 200 may be provided with holes 220 allowing e.g. grinding and/or polishing machines to apply pressure directly onto the samples 1/bases 2.

Retention of the bases 2/samples 1 in the sample holder 10 may be required in case the samples are in risk of falling off/exit the sample holder. This is likely to occur in case relatively light and/or short bases/samples 1 is mounted in the sample holder 1.

Other ways of arranging the samples 1 in the sample holder 10 may equally be applied.

The sample holder 10 may further include a stem portion 13 formed at, and extending from, a hub/center 14 of the plate 11 in a direction perpendicular to a plane defined by the plate 11.

In other not shown embodiments, the sample holder 10 may, as an alternative to the plate 11, include a plurality of arms extending from the hub 14; each arm is including a receptacle 12 for a sample 1 at one end opposite to the hub 14. A stem portion 13 is again formed at the hub/center 14, and extending from the hub/center 14 in a direction perpendicular to a plane defined by the radiating arms.

At an upper end of the stem portion 13, coupling means 15 are formed, the coupling means 15 being adapted for cooperating with not shown rotational drive means of the rinsing device 100, for example formed in the arm 102 described in connection with FIG. 5 above, the rotational drive means being configured for rotating a sample holder 10 as described below.

In one embodiment, the rotational drive means may be formed in or on a lid 120 of the rinsing device 100 or in or on an arm 102 operating the opening and closing of the lid 120. The lid 120 is adapted for cooperation with the upper edge 23 of the vessel 20, such that—in a closed position—the lid 120 covers and closes the vessel 20 to prevent any liquid contained in the vessel 21 from spilling over the upper edge 23 even if the liquid is agitated. The lid 120 may be moved between two positions—one open position, where samples 1 in a sample holder 10 may be entered into or taken out of the vessel 20 (or attached to the arm 102 and the rotational drive means), and one closed position where the lid 120 covers and closes the vessel 20. The lid 102 may be hinged to the vessel 20 or preferably to the housing 101, as shown in FIG. 5.

In other embodiments (not shown), the lid 120 may be switched between its two positions in other manners, e.g. by swinging or translational movement. In any embodiment, the lid 102 is preferably automatically moveable between its two positions by a not shown drive motor or actuator, and the operation thereof electronically controlled, e.g. by an electronic control unit (not shown) of the rinsing device 100.

In embodiments the rotational drive means (not shown) for rotating the sample holder 10 are located in an arm 102 extending from the housing 101, or from the edge 23 of the vessel 20, the lid 120 and the arm 102 being configured such that in combination they may cover and close the vessel 20 in the closed position of the lid 120.

The coupling means 15, at the upper end of the stem portion 13 of the sample holder 10, are preferably formed such that they may also cooperate with a grinding device (not shown) for grinding a plurality of samples 1 arranged in a sample holder 10. Thus, the sample holder 10 with the one or more materialographic samples may be easily transferred from the grinding device to the rinsing device and vice versa. In other embodiments (not shown), an adapter may secure that a sample holder 10 configured for either a rinsing device or a grinding device, may be transferred to the other of the two.

When the lid 120 is in its open position, a sample holder 10 may be connected to the rotational drive means. The rotational drive means are configured for rotating the sample holder 10 when the lid is closed, and in some embodiments also when the lid is closing, see below. The rotational drive means are preferably connected to and controlled by the electronic control device (not shown) of the rinsing device 100.

The rinsing device 100 further comprises a source of ultrasonic waves, i.e. ultrasound, such as an ultrasound transducer 25. The source of ultrasound is preferably arranged in the housing 101 of the rinsing device. In other embodiments, the source of ultrasound may be located in or on the vessel 20 or in or on the lid 120 or in or on the arm 102. Preferably, and as shown in FIGS. 2-4, the ultrasound source/transducer 25 is formed in the bottom 21 of the vessel 20. As shown, there can be several sources 25. In other embodiments, there may be just a single ultrasound source/transducer 25, and in yet others there may be 3, 4 or 5. Preferably, as shown in FIGS. 2-4, the ultrasound sources/transducers 25 may be placed in different positions, asymmetrically relative to the axis A.

The source of ultrasonic waves 25 is arranged in the rinsing device 100 such that one or more materialographic samples 1 in a sample holder 10 placed in the vessel 20 may be subjected to ultrasound. The source of ultrasound 25 is preferably connected to and controlled by the electronic control device of the rinsing device 100.

The rinsing device 100 further comprises means for filling and emptying the vessel 20 with a rinsing liquid.

In a preferred embodiment, the rinsing liquid is pure water, i.e. water with no additives.

The rinsing device 100 may preferably be equipped with means for connecting to a source of rinsing liquid, such as a water tap, or a rinsing liquid container being arranged in the rinsing device 100. The rinsing device 100 may further comprise pumping means (not shown) configured for pumping rinsing liquid into and/or out of the vessel 20. In other embodiments the rinsing device may be connectable to a source of pressurized rinsing liquid with the purpose of supplying the vessel. In either case a pump 105 may be provided for emptying the vessel 20. In any embodiment, any valves and/or pump or pumps are preferably connected to and controlled by the electronic control device of the rinsing device 100.

Preferably, at least one inlet 26 for rinsing liquid is provided through the bottom of the vessel 20. The inlet 26 is connected/connectable to a source of rinsing liquid as described above through a suitable piping, a rinsing liquid supply pipe 30. Preferably, the inlet 26 is provided with a deflector/water damper/flow damper 27 for deflecting the stream/jet of rinsing liquid away from a direction to parallel to the rotational axis, A, of the sample holder 10, when inserted in the vessel 20, i.e. away from a vertical axis. The deflector 27 is arranged to form a "roof" over the inlet opening. Thereby, it may be achieved that the filling of the vessel 20 with rinsing liquid may be commenced before the lid closes completely to close-of the upper open surface of the vessel 20. This may be achieved, while still providing the inlet 26 through the bottom 21 of the vessel 20, which allows for a very compact rinsing device 21.

Preferably, an outlet 28 for used rinsing liquid is also provided through the bottom 21 of the vessel 20. The outlet 28 is connected/connectable to a drain through a suitable piping, a liquid exit pipe 31, see FIG. 4, through the rinsing device 100. Thereby, the vessel 20 may be evacuated from rinsing liquid under the influence of gravity alone. However, in other embodiments, the liquid exit pipe may be connected/connectable to a vacuum source/vacuum pump 105, such as shown in FIGS. 3 and 4. Such a pump 105 is preferably connected to and controlled by the electronic control device of the rinsing device 100.

In a preferred embodiment, the inlet 26 and outlet 28, and as shown in FIGS. 2-4, is one and the same. Thereby space may be saved, and a more compact rinsing device 100 may be achieved. A valve may control the common inlet/outlet 26, 28 function. So that inlet rinsing liquid does not end in the outlet pipe 31.

In further embodiments, the rinsing device 100 may further be equipped with means for supplying alcohol or methylated spirit into the vessel 20 or more particularly spraying alcohol or methylated spirit on the materialographic samples 1 in the sample holder 10. The rinsing device 100 may preferably be equipped with means, such as an alcohol supply tube 32, for connecting to a source of alcohol or methylated spirit, such as a container being arranged in the rinsing device 100 or in connection with the rinsing device 100. The rinsing device 100 may further comprise pumping means (not shown) configured for pumping alcohol or methylated spirit into the vessel 20 from the container. In other embodiments the rinsing device may be connectable to a source of pressurized alcohol or methylated spirit. From the alcohol supply tube 32, alcohol or methylated spirit is injected into the vessel, e.g. via a nozzle 33 that may be formed in the sidewall 22 of the vessel 20. In other not shown embodiments, the nozzle 33 may be formed in the lid or in the bottom 21 of the vessel 20.

The rinsing device 100 may further be equipped with or connectable to vacuum producing means, such as a pump, for sucking out the alcohol or methylated spirit fumes from the vessel 20 via a fume outlet 29 and suitable piping. In any embodiment, any valves and/or pump or pumps are preferably connected to and controlled by the electronic control device of the rinsing device 100.

In one embodiment, not shown, the one or more outlets 28 for rinsing liquid and the one or more fume outlets 29 for alcohol or methylated spirit fumes may be the same outlet formed through the bottom 21 of the vessel 20. In this case, the outlet(s) 28, 29 is/are connected to an exit pipe 31, and the exit pipe 31 branches of in two, an upper branch 31a, through which the alcohol or methylated spirit fumes can be extracted from the rinsing apparatus 100, and a lower branch 31b, configured to evacuate the rinsing liquid from the vessel 100. The lower branch 31b may be connectable to a sewage pipe. A vacuum pump or other source of vacuum may be connected to the upper branch. As described above, the vacuum pump is preferably connected to and controlled by the electronic control device of the rinsing device 100.

In another embodiment, there is provided one outlet 28 for the rinsing liquid, in the bottom 21 of the vessel 20, and one fume outlet 29 for the alcohol or methylated spirit fumes, preferably but not necessarily formed through the sidewall 22 of the vessel 20. In the embodiment shown in FIGS. 2-4 the fume outlet 29 is formed through the sidewall 22 of the vessel 20. In this case the fume outlet 29 for the alcohol or methylated spirit fumes may be connected to an upper fume exit pipe 34, and the outlet 28 for the rinsing liquid to a lower rinsing liquid exit pipe 31, as shown in FIGS. 3 and 4. At least the upper fume exit pipe 34 may be connectable to a source of suction/vacuum, such as a pump/vacuum pump, which may be connected to and controlled by the electronic control device of the rinsing device 100. A pipe connection 35 may be provided between the upper fume exit pipe 34, and a drain pipe 40 forming an extension of the lower rinsing liquid exit pipe 31. Thus the upper fume exit pipe 34 and the outlet 29 for the alcohol or methylated spirit fumes may function as an overspill for the vessel 20, any rinsing liquid/water entering the upper fume exit pipe 34 being drained of to the lower rinsing liquid exit pipe 31 via the pipe connection 35.

In FIG. 3 the liquid exit pipe 31 is not shown. In FIG. 4 it is shown how the inlet/outlet 26/28 of FIGS. 3 and 4 may be connected to a drain by the liquid exit pipe 31. In FIG. 4 it is seen how the liquid exit pipe 31 connects to pump 105, so that the vessel may be quickly evacuated. The pump 105 is connected to a drain pipe 40 via pipe 39 forming a water lock.

In addition to any of the above mentioned embodiments the rinsing device may further be equipped with means for supplying compressed air to the inside of the vessel 20, for the purpose of drying the samples 1 in the sample holder when water has been drained from the vessel 20. The compressed air may be supplied from a ventilation unit (not shown) and the air led from ambient to the vessel through suitable piping (not shown). The piping for compressed air may be led through the vessels 20 side wall 22, through the lid, or through the bottom 21 of the vessel 20. In further embodiments the compressed air may further be heated by suitable heating means (not shown) in the compressed air piping or in the ventilation unit. The ventilation unit and/or the heating means is/are preferably connected to and controlled by the electronic control device of the rinsing device 100.

In addition to any of the above mentioned embodiments the rinsing device may further be equipped with not shown means for supplying oil to the samples 1 in the vessel 20. The oil is preferably delivered through a nozzle, connected via a suitable piping to a pressurized source of oil or source of oil connected via pump. Thereby, a mist of lubricating oil may be sprayed on the samples 1, which may be advantageous especially in the case, the materialographic samples 1 are cast iron samples. The lubrication oil will prevent or decrease oxidation. The oil nozzle and/or the oil pump are preferably connected to and controlled by the electronic control device of the rinsing device 100.

By the above mentioned embodiments of the rinsing device, it may be achieved that the rinsing device 100 may be a semi-automated stand-alone unit, where materialographic samples 1 arranged in a sample holder may be manually transferred from a grinding device to a rinsing device 100 by an operator, and once the rinsing process is initiated everything may be automatically controlled by the electronic control device of the rinsing device 100. The electronic control device of the rinsing device 100 may be configured for running various rinsing programs, which may be chosen by the operator prior to the process, and depending e.g. on the type of materialographic sample 1. When the sample 1 or samples 1 in the rinsing device 100 are dry, the sample holder 10 with the samples 1 may be removed for further grinding or for examination and further investigation.

However, in other aspects of the invention, the embodiments of the rinsing device 100, described above may be integrated with a grinding device, with e.g. a robot arm transferring the sample holder 10 between the grinding device and the rinsing device, the robot arm having means for cooperating with the coupling means 15 on the stem 13 of the sample holder 10.

In the following various embodiments of the method according to the invention will be described, with reference to the figures, and to the embodiments of the rinsing device as described above.

One method of rinsing materialographic samples 1 according to the invention involves initially arranging one or more materialographic samples 1 in a sample holder 10; the samples either comes from a grinding device, where they have been ground and therefore needs to be rinsed, or they need to be rinsed before the first grinding. The sampling holder 10 with one or more samples 1 is then coupled/ connected to a rotation head of the rinsing device 100 as described in connection with any of the embodiments above. This may be an automatic transfer, e.g. by a robotic arm as indicated above, or it may be done manually by an operator. In the latter case, the operator may then start the rinsing process e.g. by pressing a button, for example after choosing a pre-coded rinsing program stored in the electronic control unit of the rinsing device 100. Then the sample holder 10, which is now coupled to the rotation head, is entered into the vessel 20 by an actuator controlled by the electronic control unit of the rinsing device 100. Then the lid 120 is closed or starts closing. During or after closing of the lid, a number of steps are initiated: the vessel 20 starts filling up with a rinsing liquid; the rotation head starts spinning/rotating the sample holder 10 relative to the vessel 20; and the materialographic samples 1 in the sample holder 10 are subjected to ultrasonic waves, i.e. they are subjected to influence of ultrasound.

In one embodiment of the method the step of subjecting the materialographic samples 1 in the sample holder 10 to ultrasonic waves is initiated at the same time as the rinsing liquid begins to fill the vessel 20. In another embodiment, the step of subjecting the materialographic samples 1 in the sample holder 10 to ultrasonic waves is initiated before the rinsing liquid begins to fill the vessel 20. However, in a preferred embodiment, the step of subjecting the materialographic samples 1 in the sample holder 10 to ultrasonic waves is initiated during the filling of the vessel 20 with rinsing liquid. Preferably, the ultrasound is initiated within 0.5-2 seconds, such as 1 second after the filling of the vessel starts, but before the vessel 20 has been filled. Thus the ultrasound is turned on while the vessel 20 fills up. It has been found that thereby eventual dirt in the vessel 20 is loosened.

Further, the rotation of the sample holder 10, by the rotation head is initiated after the ultrasonic waves are initiated. Preferably, the rotation is initiated within 0.5-2 seconds, such as 1 second after the ultrasound influence has begun.

In any of the above embodiments the method may comprise the step of injecting said rinsing liquid through a bottom 21 of said vessel 20, where the path of said injected rinsing liquid is deflected from a direction parallel to the axis of rotation of the sample holder 10, and where the injection of rinsing liquid is initiated before a step of closing set said lid is completed.

The closing of the lid commences at the very beginning of the rinsing procedure. As each operation takes time, filling of the vessel 20 5-10 seconds, and closing of the lid 3-6 seconds, time can be saved by commencing the injection of rinsing liquid before the lid is completely closed. The rinsing liquid is preferably injected at a pressure of 2-5 bar, preferably 3 bar.

The rotations of the sample holder 10 are preferably controlled in this phase to 50-200 revolutions per minute (rpm), more preferably 50-70 rpm. This rotation in combination with the ultrasound in combination with submerging the samples into a rinsing liquid has proven very efficient in rinsing materialographic samples. In fact the method has proven so efficient that the rinsing liquid may be pure water, without any additives, such as detergents or other chemicals. Therefore, a very clean and environmentally friendly rinsing process is achieved.

In a preferred embodiment therefore the rinsing liquid is pure water. In the context of the present application, by pure water is meant tap water without any additives, such as detergents, alcohol, or organic solvents, e.g. acetone, or weak acids or basic solutions. Ultra clean water, desalinated water, or demineralized water is not necessary.

Rotation of the sample holder will result in acceleration of the rinsing liquid until it generates a vortex (vortical flow). The larger the diameter of the sample holder is—compared to the diameter of the vessel—the faster this state is established. During vortical flow, the speed of the rinsing liquid relative to the sample holder becomes very small, and therefore affects the rinsing action negatively. In order to break the vortical flow, the rotational direction may be alternated. E.g. a pattern, where the rotation is 5 seconds in one direction (e.g. clockwise), followed by 5 seconds in the opposite direction has been found useful. Further, alternations with a sequence of 2½ second intervals or 2 or 1 second has also proven efficient.

Vortical flow may also be avoided or diminished by having an asymmetrical placement of the sample holder inside the vessel, or by the use of baffles on the inside of the vessel. Each of these features may be used in addition or as alternatives to the above mentioned reversal of the rotational direction.

During application of ultrasound, the flow of the water and rotation should be kept at a rotational speed where turbulence in the liquid is minimized as this will decrease the efficiency of the ultrasound.

The ultrasound may be applied in 15-30 seconds, preferably in 18-27 seconds, such as 20-25 seconds.

The rotation is preferably applied in the above mentioned speed (and possibly in alternating direction) in 18-35 seconds, such as 20-30 seconds.

The method may further comprise the step of emptying the rinsing liquid from the vessel 20 while still rotating the sample holder 10 in the vessel 20. The rinsing liquid is drained from the vessel e.g. by opening a valve in connection with the outlet 28 whereby the outlet being formed in the bottom 21 of the vessel 20 will drain under the influence of gravity. However, in order to speed up the process, suction is applied to evacuate the vessel 20 from water.

Preferably, the ultrasound is maintained for a period after emptying the rinsing liquid is initiated. Preferably in 1-3 seconds, such as 2 seconds.

The rotational speed of the sample holder 10 is increased after the emptying of the rinsing liquid is initiated. The speed increase is commenced 2-10 seconds, such as 3-8, such as 4-7, such as 5-6 seconds the emptying of the rinsing liquid is initiated. The rotational speed is increased to 1000-3000 rpm, such as 1500-2500 rpm, such as 2000 rpm.

This speeding up of the rotation dries the samples 1 and the sample holder 10. The high speed spinning is maintained from 10 to 30 seconds, such as 15-25 seconds.

After the high speed spinning, the sample holder stops and the lid may open. Thereby the sample holder 10 with the samples 1 may be removed and placed in the grinding device or they may be removed for examination. Again this may be done automatically or manually.

In an embodiment the method further comprises the step of spraying alcohol or methylated spirit on the materialographic samples 1 in the sample holder 10 after emptying the rinsing liquid from the vessel 20.

Preferably, the step of spraying alcohol or methylated spirit on the materialographic samples 1 in the sample holder 10 is performed while rotating the sample holder 10 in the vessel 20, at the above mentioned high rotational speed, and consequently after the ultrasound is discontinued.

The spraying with alcohol or methylated spirit during the high speed rotation, helps displacing the rinsing liquid/pure water, and improves the surface tension on the samples 1 and thereby loosens any residual dirt.

The spraying with alcohol or methylated spirit may be applied for 2-8 seconds during the high speed rotation, such as 3-7 seconds, such as 4-6 seconds, such as 5 seconds.

In an embodiment the method further comprises the step of applying compressed air to the materialographic samples 1 in the sample holder 10 after emptying the rinsing liquid from the vessel 20.

Preferably, the step of applying compressed air to the materialographic samples 1 in the sample holder 10 is performed while rotating the sample holder 10 in the vessel 20, at the above mentioned high rotational speed, and consequently after the ultrasound is discontinued.

In a further embodiment the method further comprises the step of applying compressed air to the materialographic samples 1 in the sample holder 10 after the spraying alcohol or methylated spirit has ended.

The application of compressed air may be applied for 5-15 seconds during the high speed rotation, such as 10-14 seconds, such as 11-13 seconds, such as 12 seconds.

The compressed air is preferably applied at a pressure of 4-8 bar, such as 5-7 bar, such as 6 bar.

In further embodiments, the step of applying compressed aid may be continued in a short period of a few seconds after the rotation stops, such s 1-4 seconds, such as 2 seconds.

In an embodiment the method further comprises the step of spraying lubricating oil on the materialographic samples 1 in the sample holder 10 after emptying the rinsing liquid from the vessel 20. Preferably, the step of spraying lubricating oil on the materialographic samples 1 in the sample holder 10 is performed while rotating the sample holder 10 in the vessel 20, at the above mentioned high rotational speed, and consequently after the ultrasound is discontinued.

The above mentioned steps are preferably controlled by the electronic control unit of the rinsing device.

In relation to all of the above embodiments the ultrasound applied by the ultrasound sources/transducers 25 are preferably in the range of 30-150 kHz. Preferably, the ultrasound sources/transducers 25 emit ultrasound at 35 kHz. Ultrasound up to the order of 145 kHz may be used for smaller particles.

The method according to any of the above mentioned embodiments may be implemented in a device according to the embodiments of the rinsing device described further above.

The teaching of this invention has numerous advantages. Different embodiments or implementations may yield one or more of the following advantages. It should be noted that this is not an exhaustive list and there may be other advantages which are not described herein. One advantage of the teaching of this method is that it provides a great flexibility in designing and operating a rinsing or rinsing and grinding system.

Although the teaching of this application has been described in detail for purpose of illustration, it is understood that such detail is solely for that purpose, and variations can be made therein by those skilled in the art without departing from the scope of the teaching of this application.

The terms "comprising" and/or "including" as used in the claims does not exclude other elements or steps. The term "a" or "an" as used in the claims does not exclude a plurality.

The invention claimed is:

1. A method of rinsing materialographic samples comprising:
arranging one or more materialographic samples to be rinsed in a sample holder, wherein the materialographic samples comprise at least one of metal, polymer or ceramic samples that have been cut and subjected to at least one of a grinding or lapping procedure, coupling the sample holder to a rotation head of a rinsing apparatus, placing the sample holder coupled to the rotation head in a vessel of the rinsing apparatus, followed by, in a sequential order, commencing filling the vessel with a rinsing liquid by injecting the rinsing liquid through an inlet disposed in the bottom of the vessel to submerge the samples into the rinsing liquid, subjecting the rinsing liquid and the materialographic samples to ultrasound, rotating the sample holder including the materialographic samples relative to the vessel, wherein the step of subjecting the rinsing liquid and the materialographic samples to ultrasound is maintained at least during filling of the vessel with the rinsing liquid, and subjecting the rinsed materialographic samples to a second grinding, lapping or polishing procedure.

2. The method according to claim 1, wherein the rotation of the sample holder is initiated after the application of ultrasound is initiated.

3. The method according to claim 1, wherein the rotation of the sample holder is initiated after filling of the vessel with the rinsing liquid is completed.

4. The method according to claim 1, wherein application of ultrasound is commenced and maintained throughout filling of the vessel and wherein the rotation of the sample holder is initiated only after filling of the vessel is completed.

5. The method according to claim 1, wherein said rinsing apparatus includes a lid configured to move between an open position in which the materialographic samples can be placed or removed and a closed position in which the lid covers said vessel, and wherein said method further includes, prior to rotating the sample holder, moving the lid to the closed position.

6. The method according to claim 1, wherein said rinsing apparatus includes a lid configured to cover said vessel and prevent the rinsing liquid from spilling over a top surface of the vessel; and wherein said method further includes injecting said rinsing liquid through an inlet;

wherein the path of said injected rinsing liquid is deflected from a direction parallel to the axis of rotation of the sample holder; and wherein said injection of rinsing liquid is initiated before closing said lid is completed.

7. The method according to claim 1, further comprising: emptying the rinsing liquid from the vessel while rotating the sample holder including the materialographic samples.

8. The method according to claim 1, wherein the application of ultrasound is maintained while emptying the rinsing liquid from the vessel.

9. The method according to claim 1, wherein, following the arranging of one or more materialographic samples to be rinsed in the sample holder, arranging a retainer plate on top of one or more samples.

10. The method according to claim 1, wherein the method further includes spraying alcohol or methylated spirit on the materialographic samples in the sample holder after emptying the rinsing liquid from the vessel, and while rotating the sample holder in the vessel.

11. The method according to claim 1, wherein the vessel is evacuated from the rinsing liquid by applying a vacuum to an outlet of the vessel.

12. The method according to claim 1, wherein the rotational speed of the sample holder is in the range of 50-200 revolutions per minute (rpm).

13. The method according to claim 1, wherein the method includes increasing the rotational speed of the sample holder following commencement of emptying the vessel.

14. The method according to claim 1, wherein the rinsing liquid is pure water or tap water, and the method further comprises:

performing a second rinsing of the materialographic samples after the second grinding, lapping or polishing procedure.

15. The method according to claim 13, wherein the increasing the rotational speed is maintained until the rinsing process is stopped.

16. The method according to claim 13, wherein the increased rotational speed is in the range of 1,500 revolutions per minute to 2,500 revolutions per minute.

17. The method according to claim 13, wherein the method further includes simultaneously with the increasing the rotational speed of the sample holder, ventilating the vessel by application of pressurized air.

* * * * *